(12) United States Patent
Zhang et al.

(10) Patent No.: US 8,391,950 B2
(45) Date of Patent: Mar. 5, 2013

(54) SYSTEM FOR MULTI-DIMENSIONAL ANATOMICAL FUNCTIONAL IMAGING

(75) Inventors: Hongxuan Zhang, Palatine, IL (US); Jinghua Chen, Schaumburg, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 383 days.

(21) Appl. No.: 12/566,305

(22) Filed: Sep. 24, 2009

(65) Prior Publication Data
US 2010/0081917 A1 Apr. 1, 2010

Related U.S. Application Data

(60) Provisional application No. 61/101,373, filed on Sep. 30, 2008.

(51) Int. Cl.
*A61B 5/05* (2006.01)

(52) U.S. Cl. ........ 600/407; 600/410; 600/413; 600/425; 600/428

(58) Field of Classification Search ................. 600/407, 600/410, 413, 425, 428
See application file for complete search history.

(56) References Cited

U.S. PATENT DOCUMENTS

| | | | |
|---|---|---|---|
| 4,777,957 A * | 10/1988 | Wehrli et al. | 600/413 |
| 5,199,438 A | 4/1993 | Pearlman | |
| 5,229,668 A | 7/1993 | Hughes et al. | |
| 5,565,914 A | 10/1996 | Motta | |
| 5,590,649 A | 1/1997 | Caro et al. | |
| 5,778,294 A | 7/1998 | Hiraoka et al. | |
| 5,832,051 A * | 11/1998 | Lutz | 378/8 |
| 5,854,656 A | 12/1998 | Noggle | |
| 5,872,572 A | 2/1999 | Rossignac | |
| 6,032,069 A * | 2/2000 | Elgavish et al. | 600/413 |
| 6,154,516 A | 11/2000 | Heuscher et al. | |
| 6,275,560 B1 | 8/2001 | Blake et al. | |
| 6,393,091 B1 | 5/2002 | Slack et al. | |
| 6,411,740 B1 | 6/2002 | Daly et al. | |
| 6,477,553 B1 | 11/2002 | Druck | |
| 6,507,752 B1 * | 1/2003 | Maeda | 600/436 |
| 6,510,337 B1 * | 1/2003 | Heuscher et al. | 600/428 |
| 6,614,448 B1 | 9/2003 | Grlick et al. | |
| 6,708,052 B1 | 3/2004 | Mao et al. | |
| 7,031,504 B1 | 4/2006 | Argiro et al. | |
| 2005/0080336 A1 * | 4/2005 | Byrd et al. | 600/428 |
| 2006/0142984 A1 * | 6/2006 | Weese et al. | 703/11 |

* cited by examiner

*Primary Examiner* — James Kish
(74) *Attorney, Agent, or Firm* — Alexander J. Burke

(57) ABSTRACT

A cardiac functional analysis system reconstructs a 3D anatomical image volume using image frames acquired at predetermined cardiac phases over multiple cardiac cycles in response to a trigger derived from hemodynamic signals. A medical imaging system generates 3D anatomical imaging volume datasets from acquired 2D anatomical images. The system includes an image acquisition device for acquiring 2D anatomical images of a portion of patient anatomy in selectable angularly variable imaging planes in response to a synchronization signal derived from a patient blood flow related parameter. A synchronization processor provides the synchronization signal derived from the patient blood flow related parameter. An image processor processes 2D images acquired by the image acquisition device of the portion of patient anatomy in multiple different imaging planes having relative angular separation, to provide a 3D image reconstruction of the portion of patient anatomy.

20 Claims, 5 Drawing Sheets

SYSTEM FOR MULTI-DIMENSIONAL ANATOMICAL FUNCTIONAL IMAGING

This is a non-provisional application of provisional application Ser. No. 61/101,373 filed Sep. 30, 2008, by H. Zhang et al.

FIELD OF INVENTION

This invention concerns a system for generating 3D anatomical images from acquired 2D anatomical images in response to a synchronization signal derived from a patient blood flow related parameter.

BACKGROUND OF INVENTION

The evaluation of heart health status normally involves analyzing several functional characteristics of a left ventricle. These characteristics include ejection fraction, cardiac output, stroke volume, wall motion and wall thickness. The evaluation of heart health status may also include analysis of a right ventricle and atrium. Cardiac function analysis also usually involves image scanning a patient heart chamber of interest using an X-ray imaging device over multiple heart cycles. A contrast agent (dye) is injected into a patient to improve visualization of a chamber and the flow of the blood pool in and out of the chamber. The resulting images are 2D (two dimensional) X-ray frames over a time span. A physician reviews the 2D frames and picks a frame with the largest chamber volume (corresponding to an End Diastolic Phase) and a frame with the smallest chamber volume (corresponding to an End Systolic Phase). Multiple cardiac functional characteristics are computed with data from the two selected frames.

A physician visually inspects dynamic movement of contrast agent within a heart in acquired 2D frames and quantitative data is derived from the end diastolic and end systolic frames. However, the clinical evaluation of the frames may be subjective, time-consuming and requires extensive expertise and clinical experience for accurate interpretation and proper cardiac rhythm management. Additionally, continuous image scanning and data acquisition may unnecessarily expose patient tissue and organs to additional radiation. Known image scanning and acquisition systems typically employ a fixed time interval between frames and are unable to effectively scan patient anatomy and get optimum quality results for clinical monitoring and diagnosis, such as a stable and high resolution image with least exposure to radiation. A system according to invention principles addresses these deficiencies and related problems.

SUMMARY OF THE INVENTION

A cardiac functional analysis system reconstructs a 3D anatomical image volume using rotational image frames acquired at the same cardiac phase over multiple cardiac cycles in response to a trigger derived from hemodynamic signals (such as invasive blood pressure signal, blood volume calculation index). A medical imaging system generates 3D anatomical imaging volume datasets from acquired 2D anatomical images. The system includes an image acquisition device for acquiring 2D anatomical images of a portion of patient anatomy in selectable angularly variable imaging planes in response to a synchronization signal derived from a patient blood flow related parameter. A synchronization processor provides the synchronization signal derived from the patient blood flow related parameter. An image processor processes 2D images acquired by the image acquisition device of the portion of patient anatomy in multiple different imaging planes having relative angular separation, to provide a 3D image reconstruction of the portion of patient anatomy.

DETAILED DESCRIPTION OF THE INVENTION

A cardiac functional analysis system improves image quality and scanning efficiency in X-ray image acquisition using a hemodynamic signal output. The acquisition and imaging unit acquires rotational images in response to a trigger signal derived from a hemodynamic signal (such as invasive blood pressure signal, blood volume calculation index) at predefined cardiac phases over multiple cardiac cycles. Data comprising 2D images is processed to provide multiple 3D volumes, with individual volumes constructed from frames acquired at the same cardiac phase over multiple cardiac cycles. The system provides a dynamic 4D cardiac dataset series for cardiac function assessment. The system provides more efficient safer use of an imaging system (such as an X-ray image system) with less power usage and radioactivity exposure.

The system employs hemodynamic signal based image gating and acquisition using cardiac hemodynamic signals to synchronize image scanning for cardiac tissue and function monitoring and data acquisition. Hemodynamic signals, such as invasive blood pressure, non-invasive blood pressure and blood speed are used to trigger image scanning and data acquisition for cardiac function and pathology analysis. For example, the system accurately calculates and characterizes maximum volume of a chamber (such as a left ventricle) using an EoD signal (End of Diastolic pressure signal), which accurately identifies maximum volume/size of a left ventricle. The system EoD pressure based image scanning and 3D volume reconstruction advantageously enables real time monitoring (detailed monitoring during a medical procedure) and determination and prediction of cardiac tissue function and status. The system derives and calculates hemodynamic triggering and synchronizing signals such as pressure gradient, integrated pressure and pressure singularity signals (pulse signals derived and representing pressure switching, such as from atrial to ventricle).

Figure 1:
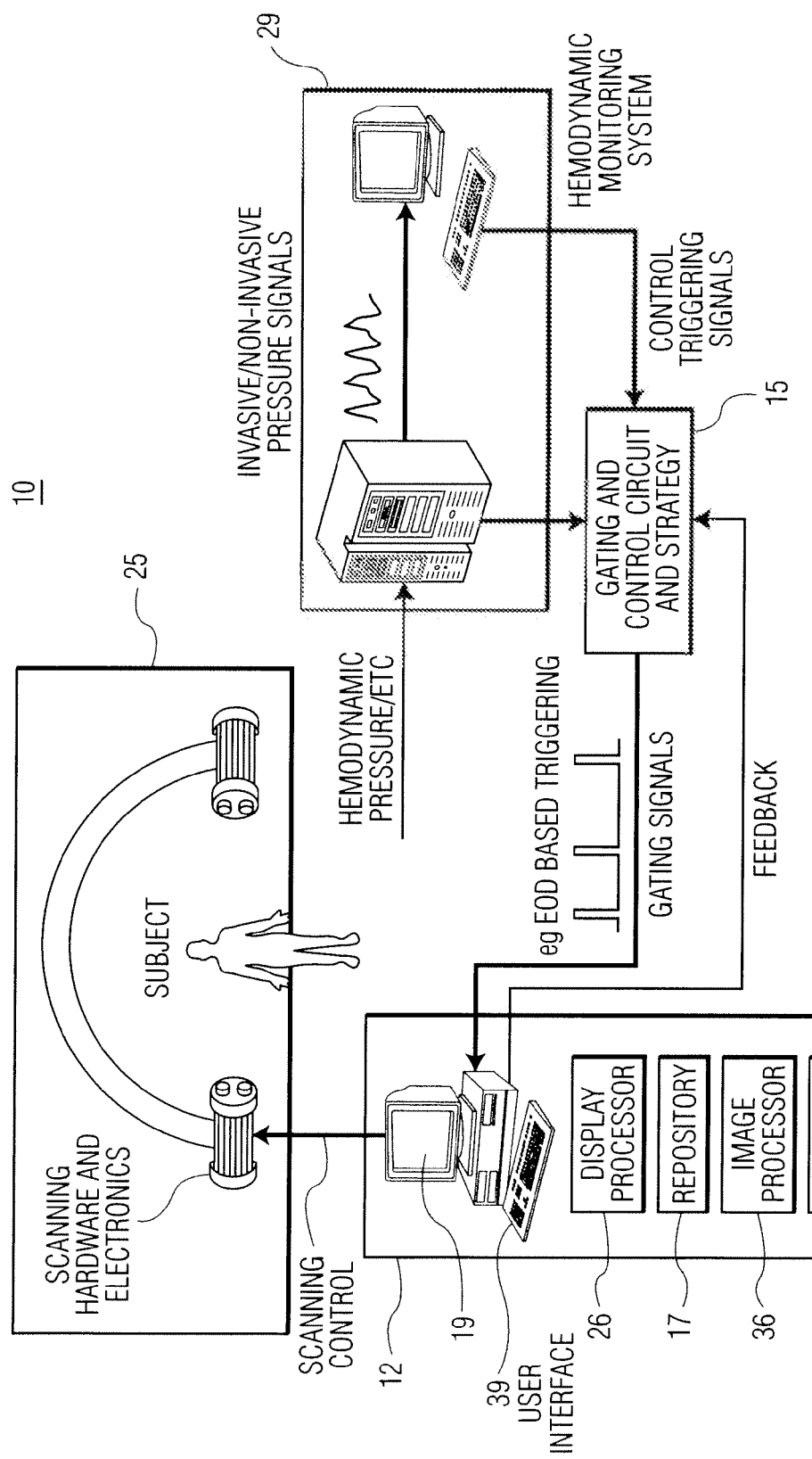
FIG. 1 shows a medical imaging system for generating 3D anatomical images from acquired 2D anatomical images, according to invention principles.

FIG. 1 shows medical imaging system 10 for generating 3D anatomical imaging volume datasets from acquired 2D anatomical images. System 10 includes one or more processing devices (e.g., workstations, computers or portable devices such as notebooks, Personal Digital Assistants) 12 that individually include at least one repository 17, image processor 36, system and imaging control unit 34 and display processor 26 presents acquired images on display 19 for review by a user. User interface 39 enables user interaction with a Graphical User Interface (GUI). Display 19 supports GUI and medical image presentation in response to predetermined user (e.g., physician) specific preferences. System 10 also includes, synchronization processor 15, patient Hemodynamic signal monitoring system 29 and imaging device 25. System and imaging control unit 34 controls operation of imaging device 25 for performing image acquisition of patient anatomy in response to user command. Imaging device 25 may comprise an X-ray imaging device (e.g., a mono-plane or biplane X-ray imaging system), a CT scanning device, MR imaging device or Ultrasound imaging system, for example. The units of system 10 intercommunicate via a network (not shown to preserve drawing clarity). At least one repository 17 stores medical image studies for patients in DICOM compatible (or other) data format. A medical image study individually includes multiple image series of a patient anatomical portion which in turn individually include multiple images.

Image scanning and acquisition unit 25 is coupled to hemodynamic signal monitoring system 29 outputting hemodynamic signals. Image acquisition device 25 acquires 2D anatomical images of a portion of patient anatomy in selectable angularly variable imaging planes in response to a synchronization signal derived from Hemodynamic signal data (e.g., a patient blood flow related parameter). Synchronization processor 15 provides the synchronization signal derived from the patient blood flow related parameter. Synchronization processor 15 monitors patient hemodynamic signals (invasive or non-invasive blood pressure signals, blood speed and acceleration signals) for multiple heart cycles, or continuously, and calculates a next optimum time when a heart chamber is at its largest volume, for example, by averaging time of occurrence of the largest volume for previous heart cycles. Synchronization processor 15 generates synchronizing signals comprising pulses for triggering acquisition of rotational images in response to a calculated next time of occurrence of a largest chamber volume within an image scanning cycle. At the start of acquisition of rotational images, device 25 is resynchronized with hemodynamic signals. Device 25 acquires rotational images over a few heart cycles at a time stamp (from start of respective heart cycles) identifying a calculated next time of occurrence of a largest chamber volume in response to a synchronization signal comprising a recorded hemodynamic signal. For example, by using ED (end of diastolic pressure) and ES (end of systolic pressure), the maximum and minimum volume of the ventricle is acquired and parameters such as ejection volume are calculated.

Image processor 36 processes 2D images acquired by image acquisition device 25 of the portion of patient anatomy in multiple different imaging planes having relative angular separation, to provide a 3D image reconstruction of the portion of patient anatomy. A feedback signal is provided by processing device 12 to generator 15 to compensate for circuit and processing delay to ensure accuracy of timing of image acquisition. Image processor 36 provides image data processing including mapping of image points to a location and time corresponding to a 3D imaging volume representation of a heart position and registration (alignment) of different images to support heart condition diagnosis.

Invasive or non-invasive hemodynamic (pressure) signals are acquired from a patient by hemodynamic signal monitoring system 29 and used by synchronization processor 15 to generate synchronization and triggering (gating) signals for image scanning using image acquisition device 25. Invasive hemodynamic signals include intra-cardiac chamber or vessel pressure signals. Non-invasive hemodynamic signals include external blood pressure signals. The hemodynamic signals are used for patient status monitoring and provide information to the image system identifying volume changes, blood filling and ejection, for example. An X-ray system may include a moveable C-arm mounting an X-ray emitter at one end and an X-ray detector at the other end enabling multi-angle, multi-speed, and multi-channel real time scanning and image construction in multiple dimensions for multi-dimensional image monitoring of a left ventricle and other features.

System 10 acquires images in response to a time stamp (indicating time within a heart cycle from a designated cycle start point) and synchronized with trigger signals derived by unit 15 from blood pressure signals. Hence system 10 accurately acquires a time stamped image such as a heart image at EoD time (end of diastolic time) or chamber filling start time, for example. Images with the same cardiac function time stamp are acquired from multiple sequential (consecutive or non-consecutive) heart cycles enabling identification of cardiac function change beat by beat. System 10 provides automatic hemodynamic parameter (pressure) based image acquisition for cardiac function imaging and analysis. The hemodynamic signal based imaging aids prevention of unnecessary image scanning and acquisition, such as at incompatible times (different points within a heart cycle) resulting in incompatible comparison images. The system reduces redundant image scanning and reduces patient radiation exposure.

The system enables a physician to more accurately analyze heart function and increases physician confidence in a diagnosis corroborated with improved image accuracy. System 10 uses X-ray images accurately representing the shape and the size of a heart at a particular phase of the heart cycle acquired with a hemodynamic signal trigger, to construct multiple 3D image volume datasets. The multiple 3D image volume dataset time series (or 4D dataset comprising a time series of individual 3D volume datasets at sequential times within a heart cycle) gives a physician a more intuitive and direct view of heart movement and contraction. In addition, system 10 uses a hemodynamic signal trigger to synchronize acquisition of an image of a heart chamber at maximum volume to improve quantitative analysis of heart function.

Known imaging systems provide X-ray angiograms of heart chambers comprising contrast enhanced 2D frames over a time period. Known systems support rotating a C-Arm during image acquisition so that multiple 2D frames from different projections can be used to reconstruct a single 3D volumetric image. Though a single 3D volumetric image is helpful to physicians, it does not show the dynamic movement of the heart in 3D and real time. In contrast system 10 advantageously uses selected 2D frames from the same phase (same time stamp for each heart beat cycle) of several heart cycles to construct a 3D volume image. This ensures minimal distortion and improved accuracy of a 3D imaging volume because each 2D frame selected represents the heart with the same shape, size and orientation. The resulting images comprise a 4D cardiac sequence that shows a physician heart dynamics in 3D space with time stamping in a stable and reliable manner.

Synchronization processor 15 employs different triggering methods for use in obtaining an X-ray angiogram, such as using ECG signals to acquire images when a heart is in its least motion phase. This can help to acquire an image with good motion tolerance. Retrospective ECG gating is used in order to automatically select a largest heart chamber volume frame from acquired frames. This involves recording ECG signals concurrently with image acquisition. During analysis of an image sequence, a frame that corresponds to the time point at which an ECG indicates the end diastolic phase is selected as frame showing a largest left ventricle volume. However, an image acquisition sequence initiated at an arbitrary time point may fail to capture an image of a heart chamber at maximum volume as this may fall between X-ray acquisition trigger pulses. The resulting acquired sequence does not contain a frame of the heart chamber at its physical maximum volume. Also, an ECG signal does not correlate well with volume change of a heart and is best used for detecting a motionless heart phase. In contrast, generator 15 derives an image acquisition trigger signal from a hemodynamic signal instead of an ECG signal, to take advantage of the stable relationship between a hemodynamic signal and heart volume change. Furthermore, by using the hemodynamic signal to synchronize the start time of an image acquisition sequence, system 10 arranges the moment of largest heart volume to be substantially more likely to coincide with an X-ray pulse for image scanning.

System 10 provides accurate cardiac functional parameter calculation using hemodynamic signal synchronization to determine maximum volume of heart chambers using a trigger signal derived from invasive blood pressure and performs cardiac function evaluation based on the tissue contraction speed, for example. System 10 also performs real time 3D and multi-dimensional image monitoring by reconstructing 3D imaging volumes from 2D images having the same intra-heart cycle time stamp (the time also accurately identifies hemodynamic functions such as diastolic and systolic pressure cycle points). System 10 improves efficiency of imaging whilst minimizing radioactivity exposure in performing continuous X-ray image acquisition by advantageously integrating imaging device 25 and hemodynamic signal monitoring system 29. System 10 performs real time multi-dimensional imaging and derives a temperature or energy parameter used for cardiac function analysis and diagnosis. System 10 maps a derived temperature or energy parameter, for example, to a medical condition using predetermined mapping information stored in repository 17 associating predetermined medical conditions with predetermined parameter value ranges. System 10 also adaptively adjusts speed of image scanning and acquisition in response to heart and tissue contraction and movement data associated with cardiac systolic and diastolic phases, for example.

Pressure signals including invasive and non-invasive hemodynamic signals are used to quantify and characterize status and severity of cardiac functions and tissue. Hemodynamic signals are used as (or for deriving) synchronizing trigger signals to trigger medical device working sequences, for example, to provide image scanning at different heart cycle phases for cardiac function comparison (such as of a blood filing procedure and blood ejection procedure).

Figure 2:
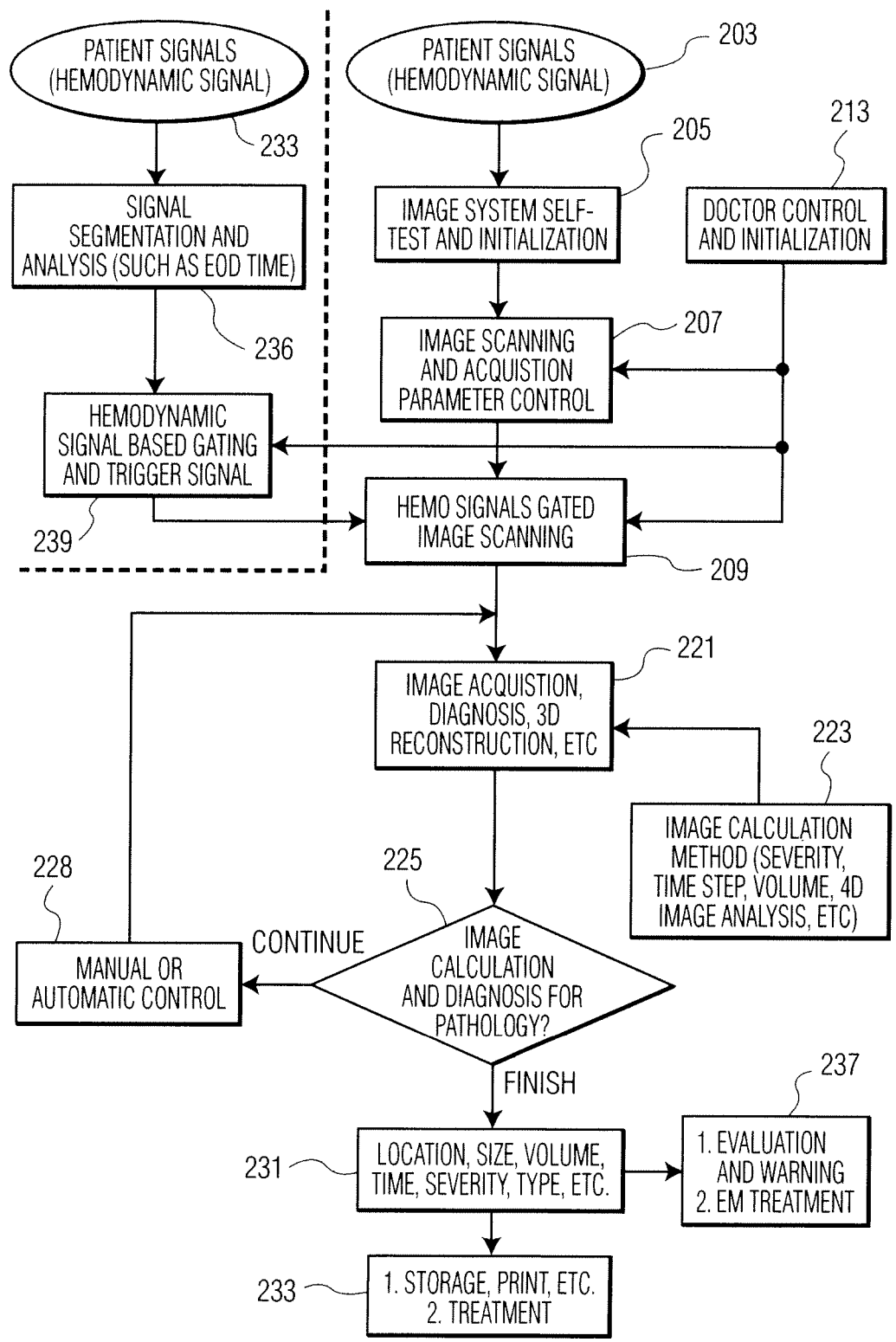
FIG. 2 shows a process and workflow of Hemodynamic signal based image gating and acquisition employed by an image acquisition system, according to invention principles.

FIG. 2 shows a process and workflow of Hemodynamic signal based image gating and acquisition employed by image acquisition system 10 (FIG. 1). System 10 image scanning and acquisition parameters are adaptively selected and adjusted. Hemodynamic signal monitoring system 29 acquires, buffers and digitizes hemodynamic signals in step 203 and applies the signals for initializing and testing imaging device 25 in step 205. Image scanning and acquisition parameters including image resolution and scanning rate that vary over the duration of one or more heart cycles are adaptively determined and set in step 207. These parameters are set in response to predetermined selected configuration data of a physician or configuration data associated with a particular clinical procedure, diagnosis or imaging characteristics, and data indicating a type of clinical procedure and/or user entered data and commands provided in step 213. Similarly, in step 233, Hemodynamic signal monitoring system 29 acquires, buffers and digitizes hemodynamic signals and patient blood flow related parameters in step 233 for processing in step 236 to derive heart cycle segment representative signals and signals identifying EoD (End of Diastolic) and EoS (End of Systolic) points in a heart cycle and signals indicative of other portions of blood pressure and respiratory signals, for example. Synchronization processor 15 (FIG. 1) in step 239 (FIG. 2) adaptively derives a trigger signal in response to predetermined selected configuration data of a physician or configuration data associated with a particular clinical procedure, or data indicating a type of clinical application and procedure acquired in step 213. Synchronization processor 15 provides a synchronization signal comprising a patient hemodynamic signal itself (waveform or sync pulse). Synchronization processor 15 also provides a synchronization signal using patient blood flow related parameters by adaptively deriving a trigger comprising a non-periodic sequence of pulses using data representing at least one of, invasive blood pressure, non-invasive blood pressure, blood flow rate, flow acceleration, gradient signals, energy, spectrum, dominant amplitude and dominant frequency of hemodynamic signal components. Synchronization processor 15 in one embodiment, also uses vital signs signals (blood oxygen saturation SPO2, respiration blood pressure acceleration) signals in generating the synchronization signal.

Image acquisition device 25 in step 209 performs X-ray (or other) image acquisition gated and synchronized using trigger signals comprising non-periodic sequence of pulses derived in step 239 and in response to predetermined selected configuration data of a physician or configuration data associated with a particular clinical procedure, or data indicating a type of clinical application and procedure acquired in step 213. System 10 tunes image scanning and acquisition (of uni-plane or bi-plane X-ray system 25) based on the signals and data acquired in step 213, to obtain an optimum image for a specific application such as for maximum chamber volume calculation with motion noise rejection. Image acquisition device 25 adapts image resolution, image sensitivity, radiation exposure time, and imaging device operational speed, of at least one image of multiple images in response to multiple individual pulses of the non-periodic sequence of pulses. Two dimensional (2D) X-ray images acquired by acquisition device 25 are processed in step 221 to reconstruct a 3D imaging volume dataset and 4D dataset using the 3D dataset and facilitate qualitative and quantitative diagnosis and characterization of abnormal cardiac functions and pathologies. In step 223 image processor 36 selects a process to use for analysis of an acquired image to determine, medical condition, severity, time step used between image acquisition, chamber volume and to derive a 3D and 4D image reconstruction from 2D images, for example. Selectable processes include a process for chamber edge determination for maximum chamber area and volume analysis and image registration for vessel and chamber analysis.

In step 225 image processor 36 uses a selected process to analyze an acquired image to determine image associated parameters and calculate image associated values and identify a particular medical condition by mapping determined parameters and calculated values to corresponding value ranges associated with medical conditions using predetermined mapping information stored in repository 17. Processor 36 also determines medical condition severity, chamber volume and derives 3D and 4D image reconstructions from 2D images, for example. Steps 221 and 225 are iteratively repeated in response to manual or automatic direction in step 228 to identify medical condition characteristics in one or more different acquired images. In response to completion of iterative image analysis of steps 221, 225 and 228, processor 36 in step 231 determines location, size, volume, severity and type of medical condition as well as a time within a heart cycle associated with a medical condition. Processor 36 initiates generation of an alert message for communication to a user in step 237 and provides medical information for use by a physician in making treatment decisions. Display processor 26 in step 233 presents images, acquired by acquisition device 25 to a user on a reproduction device such as display 19 or a printer and stores images in repository 17 and prompts a user with mapped treatment suggestions.

Figure 3:
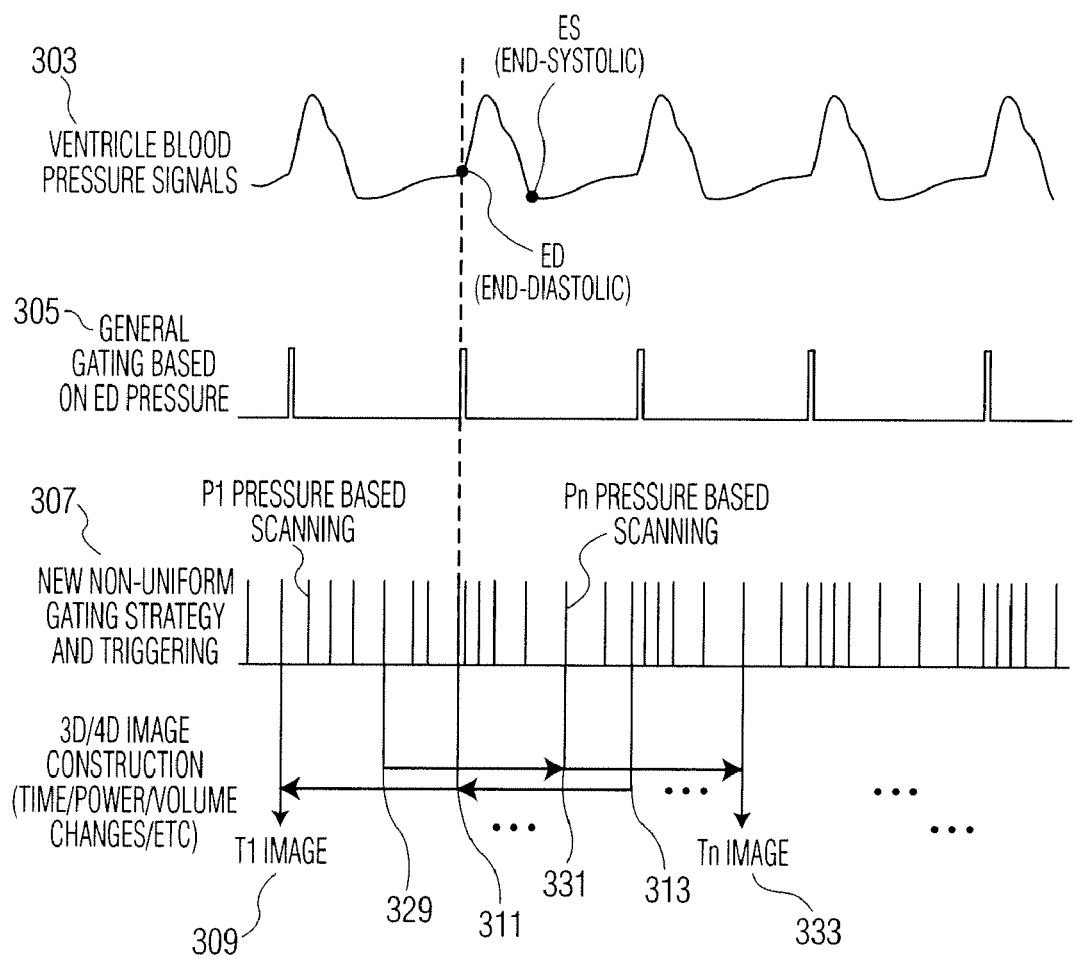
FIG. 3 shows non-uniform, non-periodic arrangements of pulses derived from a Hemodynamic signal and used for triggering image acquisition in an image acquisition system, according to invention principles.

FIG. 3 shows non-uniform, non-periodic arrangements of pulses derived from a Hemodynamic signal and used for triggering image acquisition by device 25. Invasive blood pressure (measured by a hemodynamic signal) is typical used for monitoring the internal blood pressure of cardiac chambers. FIG. 3 illustrates image acquisition involving invasive blood pressure of a left ventricle. Generator 15 generates a synchronization signal for non-uniform image scanning control and adjustment for multi dimensional image construction (3D, 4D) and to derive associated parameters including heart cycle segment time stamps, power, temperature, energy, and variance of derived parameters. Pressure waveform 303 shows systolic and diastolic pressure switching within a cardiac cycle and reflects the changes occurring within heart tissue activity. During a systolic stage, cardiac tissue is in a squeezing mode and there is substantial heart movement for which synchronization processor 15 generates non-uniform, non-periodic sequence of pulses 307 using ED pressure gating signal 305. During a diastolic stage, cardiac tissue is in a relatively relaxed mode with blood filling a heart chamber and there is less heart movement for which synchronization processor 15 generates non-uniform, non-periodic pulse sequence 307 (using derived ED pressure gating signal 305) to trigger relatively slow image scanning and data acquisition, for example. The hemodynamic based synchronization signal is used capture images at different pressure values (such as P1 to Pn indicated in pulse sequence 307) including of systolic and diastolic procedures.

Image processor 36 processes 2D images acquired by image acquisition device 25 by selecting image frames that are acquired at a same heart cycle point (time stamp) at different angulations in response to a synchronization signal, to reconstruct a single 3D volume of a portion of patient anatomy. System 10 sorts multiple acquired imaging datasets representing 3D volumes based on heart cycle phase sequence. Image processor 36 selects images acquired at the same cycle points in sequential heart cycles (consecutive or non-consecutive) to generate a 3D imaging volume dataset. Specifically, processor 36 selects images at points 309, 311 and 313 acquired in response to synchronization signal 307 provided by generator 15 to form a first 3D volume imaging dataset and selects images at points 329, 331 and 333 acquired in response to synchronization signal 307 to form a second 3D volume imaging dataset.

Figure 4:
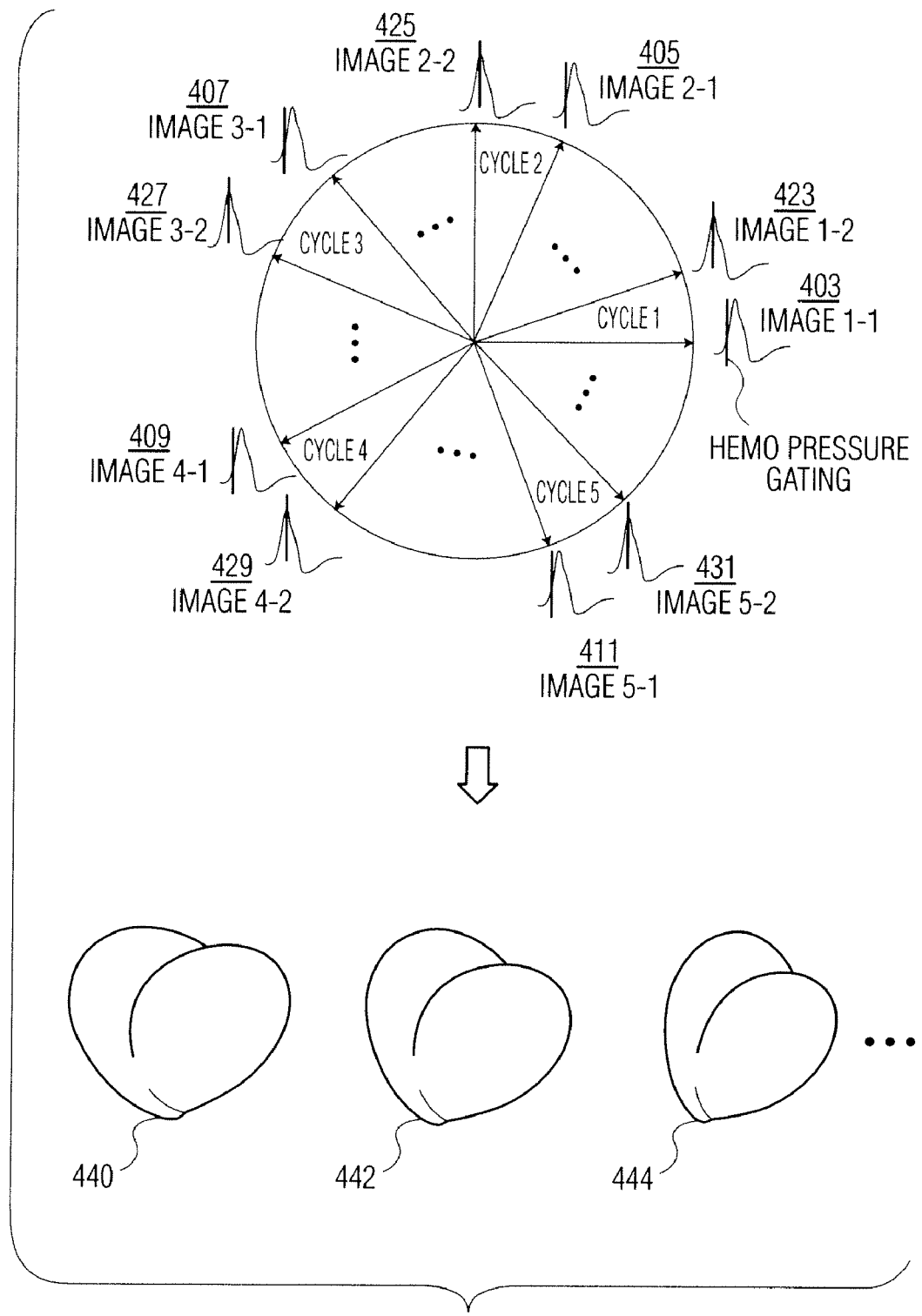
FIG. 4 illustrates multi-dimension heart image reconstruction based on non-uniform, non-periodic Hemodynamic signal gated image scanning and acquisition, according to invention principles.

FIG. 4 illustrates multi-dimension heart image reconstruction based on non-uniform, non-periodic Hemodynamic signal gated image scanning and acquisition. Ancillary image information including cardiac wall thickness, temperature, signal energy, for example, is mapped to a corresponding tissue location in a 3D constructed image transforming a 3D volume dataset to a 4D image volume dataset (or higher dimension image dataset) in a real time manner. Thereby system 10 captures and displays detailed information during an imaging or interventional procedure without significant time delay. System 10 acquires images at the same time having the same time stamp in a heart cycle as indicated by a synchronization signal derived from a hemodynamic signal by generator 15 (FIG. 1). Image processor 36 constructs a real time 3D image volume using 2D images acquired in different heart cycles but having the same time stamp point relative to start of a heart cycle. Image processor 36 advantageously reconstructs 3D image volumes 440, 442 and 444 using synchronized images to improve 3D image quality. Imaging device 25 (FIG. 1) acquires 2D images at the same time position within individual heart beat cycles and under the same conditions of patient movement in response to a trigger signal provided by synchronization processor 15. Thereby images are acquired from different angles of the heart to provide high precision 3D image reconstruction.

Synchronization processor 15 employs precise heart cycle phase timing for individual image acquisition to ensure high pixel resolution and reliability of 3D image reconstruction. Processor 36 uses multiple sets of images acquired at multiple different points in a heart cycle to generate 3D image reconstructions 440, 442 and 444 with an individual set of images being acquired at a particular point in a heart cycle determined by the trigger signal. Specifically, processor 36 generates 3D image reconstructions 440 and 442, for example, using first and second 2D (two dimensional) image sets, respectively. The first image set includes images acquired at substantially the same first point within five sequential (consecutive or non-consecutive) heart cycles (points 403, 405, 407, 409 and 411) gated by the trigger signal provided by generator 15 at a first particular phase of a heart cycle (having substantially the same first time stamp). The second image set includes multiple 2D images including images acquired at a second point within five sequential (consecutive or non-consecutive) heart cycles (points 423, 425, 427, 429 and 431) gated by the trigger signal provided by generator 15 at a second particular phase of a heart cycle (having substantially the same second time stamp). Processor 36 uses 2D images in reconstruction having substantially the same time stamp to minimize tissue distortion and motion effects to produce a 3D (or 4D) image volume dataset that facilitates detection of cardiac changes and abnormality. In addition, image processor 36 adaptively generates a 3D imaging volume by replacing older image frames with newly acquired images to provide a continuous real time 3D volume to support diagnosis and treatment.

Figure 5:
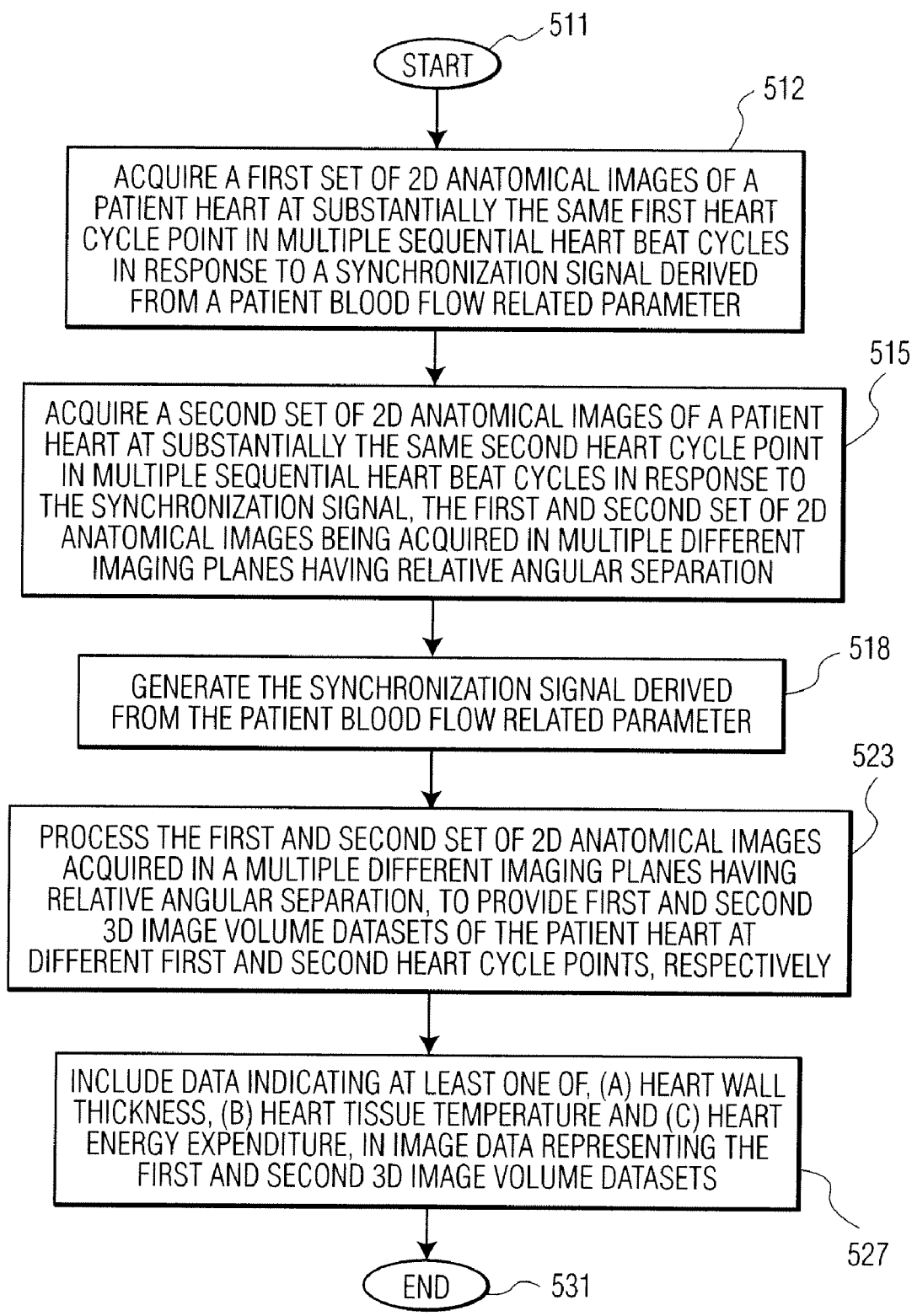
FIG. 5 shows a flowchart of a process used by a medical imaging system for generating 3D anatomical images from acquired 2D anatomical images, according to invention principles.

FIG. 5 shows a flowchart of a process used by medical imaging system 10 for generating 3D anatomical images from acquired 2D anatomical images. In step 512 following the start at step 511, image acquisition device 25 acquires a first set of 2D anatomical images of a patient heart at substantially the same first heart cycle point in multiple sequential heart beat cycles in response to a synchronization signal derived from a patient blood flow related parameter. In step 515, device 25 acquires a second set of 2D anatomical images of a patient heart at substantially the same second heart cycle point in multiple sequential heart beat cycles in response to the synchronization signal. Device 25 acquires the first and second sets of 2D anatomical images by acquiring images at first and second time stamps respectively, relative to a point in a heart cycle. The first and second set of 2D anatomical images are acquired in multiple different imaging planes having relative angular separation in two or three dimensions, for example. Image acquisition device 25 acquires multiple 2D anatomical images of a patient heart in substantially the same operational phase over multiple heart beat cycles in response to the synchronization signal derived from the patient blood flow related parameter and synchronizes image acquisition to heart phases including a phase at which heart volume is a minimum or a phase at which heart volume is a maximum, for example. The same operational phase comprises at least one of, (a) an end of diastolic pressure (ED) phase and (b) an end of systolic pressure (ES) phase.

Synchronization processor 15 in step 518 provides the synchronization signal derived from the patient blood flow related parameter by generating synchronization pulses at first and second time stamps relative to a point in a heart cycle respectively. The patient blood flow related parameter indicates at least one of, (a) invasive blood pressure, (b) non-invasive blood pressure, (c) blood flow velocity and (d) blood flow acceleration. In one embodiment, the synchronization signal is derived from parameter data derived from a patient blood flow related parameter such as a blood pressure gradient indicator.

In step 523 image processor 36 processes the first and second set of 2D anatomical images acquired in multiple different imaging planes having relative angular separation, to provide first and second 3D image volume datasets of the patient heart at different first and second heart cycle points, respectively. Image processor 36 processes multiple 2D anatomical images of the patient heart in substantially the same operational phase over multiple heart beat cycles to provide a 3D image reconstruction of the heart in the same operational phase. Image processor 36 calculates a maximum left ventricle volume, minimum left ventricle volume and an ejection fraction value based on image data acquired at the same heart operational phase. Image processor 36 in step 527 includes data indicating at least one of, (a) heart wall thickness, (b) heart tissue temperature and (c) heart energy expenditure, in image data representing the first and second 3D image volume datasets. The process of FIG. 5 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system employs a synchronization signal derived from a hemodynamic signal to trigger 2D imaging at predefined cardiac phases over multiple cardiac cycles and processes 2D images to provide multiple 3D volumes and a dynamic 4D cardiac dataset series for cardiac function assessment. Further, the processes and applications may, in alternative embodiments, be located on one or more (e.g., distributed) processing devices on the network of FIG. 1. Any of the functions and steps provided in FIGS. 1-5 may be implemented in hardware, software or a combination of both.

What is claimed is:

1. A medical imaging system for generating 3D anatomical imaging volume datasets from acquired 2D anatomical images, comprising:

an image acquisition device for acquiring 2D anatomical images of a portion of patient anatomy in selectable angularly variable imaging planes in response to a synchronization signal derived from a patient blood flow related amplitude parameter signal;

a synchronization processor for providing said synchronization signal derived from said patient blood flow related amplitude parameter signal by, in response to data indicating a type of clinical application, adaptively deriving at least one of, (a) a signal derived from a patient blood pressure signal and comprising at least one of, (i) an end of diastolic pressure (ED) phase signal and (ii) an end of systolic pressure (ES) phase signal and, (b) a patient blood flow acceleration signal, said synchronization processor provides said synchronization signal derived from amplitude of said patient blood pressure signal; and an image processor for processing 2D images acquired by said image acquisition device of said portion of patient anatomy in a plurality of different imaging planes having relative angular separation, to provide a 3D image reconstruction of said portion of patient anatomy.

2. A system according to claim 1, wherein
said image acquisition device acquires a first set of 2D anatomical images of a patient heart at substantially the same first heart cycle point in a plurality of sequential heart beat cycles and acquires a second set of 2D anatomical images of a patient heart at substantially the same second heart cycle point in a plurality of sequential heart beat cycles in response to said synchronization signal derived from said patient blood flow related parameter signal,
said image processor processes the first and second set of 2D anatomical images to provide first and second 3D image volume datasets of the patient heart respectively and
said angularly variable imaging planes are variable in two dimensions.

3. A system according to claim 1, wherein
said image acquisition device acquires said 2D images in response to a time stamp indicating time within a heart cycle from a designated cycle start point and synchronized with said synchronization signal.

4. A system according to claim 1, wherein
said patient blood flow related parameter signal comprises a blood pressure gradient indicator and
said synchronization signal comprises a patient blood flow velocity signal.

5. A system according to claim 1, wherein
said image acquisition device acquires a plurality of 2D anatomical images of a patient heart in substantially the same operational phase over a plurality of heart beat cycles, in response to said synchronization signal derived from said patient blood flow related parameter signal and synchronizing image acquisition to heart phases including at least one of, (a) a phase at which heart volume is a minimum and (b) a phase at which heart volume is a maximum.

6. A medical imaging system for generating 3D anatomical imaging volume datasets from acquired 2D anatomical images, comprising:
an image acquisition device for acquiring 2D anatomical images of a portion of patient anatomy in selectable angularly variable imaging planes in response to a synchronization signal derived from a patient blood flow related parameter signal;
a synchronization processor for providing said synchronization signal derived from said patient blood flow related amplitude parameter signal by, in response to data indicating a type of clinical application, adaptively deriving at least one of,
  (a) a signal derived from a patient blood pressure signal and substantially comprising at least one of, (i) an end of diastolic pressure (ED) phase indicative signal and (ii) an end of systolic pressure (ES) phase indicative signal and,
  (b) a patient blood flow acceleration signal; and
an image processor for processing 2D images acquired by said image acquisition device of said portion of patient anatomy in a plurality of different imaging planes having relative angular separation, to provide a 3D image reconstruction of said portion of patient anatomy wherein
said synchronization processor provides said synchronization signal derived from a dominant frequency of said patient blood pressure signal and
said angularly variable imaging planes are variable in three dimensions.

7. A medical imaging system for generating 3D anatomical imaging volume datasets from acquired 2D anatomical images, comprising:
an image acquisition device for acquiring 2D anatomical images of a portion of patient anatomy in selectable angularly variable imaging planes in response to a synchronization signal derived from a patient blood flow related parameter signal;
a synchronization processor for providing said synchronization signal derived from said patient blood flow related parameter signal by, in response to data indicating a type of clinical application, adaptively deriving at least one of,
  (a) a signal derived from a patient blood pressure signal and substantially comprising at least one of, (i) an end of diastolic pressure (ED) phase indicative signal and (ii) an end of systolic pressure (ES) phase indicative signal and,
  (b) a patient blood flow acceleration signal; and
an image processor for processing 2D images acquired by said image acquisition device of said portion of patient anatomy in a plurality of different imaging planes having relative angular separation, to provide a 3D image reconstruction of said portion of patient anatomy wherein
said synchronization processor provides said synchronization signal derived from a dominant amplitude of said patient blood pressure signal and
said patient blood pressure signal comprises at least one of, (a) an invasive blood pressure signal, and (b) a non-invasive blood pressure signal.

8. A medical imaging system for generating 3D anatomical imaging volume datasets from acquired 2D anatomical images, comprising:
an image acquisition device for acquiring 2D anatomical images of a portion of patient anatomy in selectable angularly variable imaging planes in response to a synchronization signal derived from a patient blood flow related parameter signal;
a synchronization processor for providing said synchronization signal derived from said patient blood flow related parameter signal by, in response to data indicating a type of clinical application, adaptively deriving at least one of,
  (a) a signal derived from a patient blood pressure signal and substantially comprising at least one of, (i) an end of diastolic pressure (ED) phase indicative signal and (ii) an end of systolic pressure (ES) phase indicative signal and,
  (b) a patient blood flow acceleration signal; and
an image processor for processing 2D images acquired by said image acquisition device of said portion of patient anatomy in a plurality of different imaging planes having relative angular separation, to provide a 3D image reconstruction of said portion of patient anatomy wherein
said image acquisition device acquires a plurality of 2D anatomical images of a patient heart in substantially the same operational phase over a plurality of heart beat cycles in response to said synchronization signal derived from said patient blood flow related parameter signal and said image processor replaces older images of said 2D images with newly acquired images to provide a continuous real time 3D volume image reconstruction.

9. A system according to claim 8, wherein
said same operational phase comprises at least one of, (a) an end of diastolic pressure (ED) phase and (b) an end of systolic pressure (ES) phase.

10. A system according to claim 9, wherein
said image processor calculates at least one of maximum left ventricle volume and minimum left ventricle volume based on image data acquired at said same operational phase.

11. A system according to claim 9, wherein
said image processor calculates an ejection fraction value based on image data acquired at said same operational phase.

12. A system according to claim 8, wherein
said image processor processes said plurality of 2D anatomical images of said patient heart in substantially the same operational phase over said plurality of heart beat cycles to provide a 3D image reconstruction of said heart in said same operational phase.

13. A system according to claim 12, wherein
said image processor incorporates data indicating at least one of, (a) heart wall thickness, (b) heart tissue temperature and (c) heart energy expenditure, in image data representing said 3D image reconstruction of said heart in said same operational phase.

14. A method employed by a medical imaging system for generating 3D anatomical imaging volume datasets from acquired 2D anatomical images, comprising the activities of:
acquiring a first set of 2D anatomical images of a patient heart at substantially the same first heart cycle point in a plurality of sequential heart beat cycles in response to a synchronization signal derived from a patient blood flow related parameter signal;
acquiring a second set of 2D anatomical images of a patient heart at substantially the same second heart cycle point in a plurality of sequential heart beat cycles in response to said synchronization signal;
generating said synchronization signal derived from said patient blood flow related parameter signal by, in response to data indicating a type of clinical application, adaptively deriving at least one of,
 (a) a signal derived from a patient blood pressure signal and substantially comprising at least one of, (i) an end of diastolic pressure (ED) phase indicative signal and (ii) an end of systolic pressure (ES) phase indicative signal and,
 (b) a patient blood flow acceleration signal, said synchronization signal being derived from a dominant amplitude of said patient blood pressure signal; and
processing the first and second set of 2D anatomical images to provide first and second 3D image volume datasets of the patient heart at different first and second heart cycle points, respectively.

15. A method according to claim 14, wherein
said first and second set of 2D anatomical images are acquired by an image acquisition device in a plurality of different imaging planes having relative angular separation and
said angularly variable imaging planes are variable in two dimensions.

16. A method according to claim 14, wherein
said activities of acquiring said first and second sets of 2D anatomical images comprise acquiring images at first and second time stamps relative to a point in a heart cycle respectively and including the activity of
replacing older images of said 2D images with newly acquired images to provide a continuous real time 3D volume image reconstruction.

17. A method according to claim 14, wherein
said activity of generating said synchronization signal comprises generating synchronization pulses at first and second time stamps relative to a point in a heart cycle respectively and including the activity of
generating said synchronization signal derived from a dominant frequency of said patient blood pressure signal.

18. A method according to claim 14, including the activity of
including data indicating at least one of, (a) heart wall thickness, (b) heart tissue temperature and (c) heart energy expenditure, in image data representing said first and second 3D image volume datasets.

19. A medical imaging system for generating 3D anatomical imaging volume datasets from acquired 2D anatomical images, comprising:
an image acquisition device for,
 acquiring a first set of 2D anatomical images of a patient heart at substantially the same first heart cycle point in a plurality of sequential heart beat cycles in response to a synchronization signal derived from a patient blood flow related parameter signal and
 acquiring a second set of 2D anatomical images of a patient heart at substantially the same second heart cycle point in a plurality of sequential heart beat cycles in response to said synchronization signal, the first and second set of 2D anatomical images being acquired in a plurality of different imaging planes having relative angular separation;
a synchronization processor for providing said synchronization signal derived from said patient blood flow related parameter signal by, in response to data indicating a type of clinical application, adaptively deriving at least one of,
 (a) a signal derived from a patient blood pressure signal and substantially comprising at least one of, (i) an end of diastolic pressure (ED) phase indicative signal and (ii) an end of systolic pressure (ES) phase indicative signal and,
 (b) a patient blood flow acceleration signal; and
an image processor for processing the first and second set of 2D anatomical images acquired in a plurality of different imaging planes having relative angular separation, to provide first and second 3D image volume datasets of the patient heart at different first and second heart cycle points, respectively, wherein said image acquisition device acquires a plurality of 2D anatomical images of a patient heart in substantially the same operational phase over a plurality of heart beat cycles in response to said synchronization signal derived from said patient blood flow related parameter signal and said image processor replaces older images of said 2D images with newly acquired images to provide a continuous real time 3D volume image reconstruction.

20. A system according to claim 19, wherein
said image acquisition device comprises one of, (a) a mono-plane X-ray imaging system (b) a biplane X-ray imaging system, (c) a CT image scanning system, (d) an MR imaging system and (e) an Ultrasound imaging system.

* * * * *